United States Patent
Boes (10) Patent No.: US 11,034,665 B2
(45) Date of Patent: Jun. 15, 2021

(54) COMPOUNDS USEFUL AS POTASSIUM CHANNEL OPENERS

(71) Applicant: ACOUSIA THERAPEUTICS GMBH, Tuebingen (DE)

(72) Inventor: Michael Boes, Tuebingen (DE)

(73) Assignee: Acousia Therapeutics GmbH, Tuebingen (DE)

( * ) Notice: Subject to any disclaimer, the term of this patent is extended or adjusted under 35 U.S.C. 154(b) by 0 days.

(21) Appl. No.: 16/487,933

(22) PCT Filed: Feb. 27, 2018

(86) PCT No.: PCT/EP2018/054820
§ 371 (c)(1),
(2) Date: Aug. 22, 2019

(87) PCT Pub. No.: WO2018/158256
PCT Pub. Date: Sep. 7, 2018

(65) Prior Publication Data
US 2020/0157072 A1    May 21, 2020

(30) Foreign Application Priority Data
Feb. 28, 2017 (EP) .................................. 17158326

(51) Int. Cl.
*A61P 27/16* (2006.01)
*C07C 323/63* (2006.01)
*C07D 333/28* (2006.01)
*C07D 409/12* (2006.01)

(52) U.S. Cl.
CPC ............ *C07D 333/28* (2013.01); *A61P 27/16* (2018.01); *C07C 323/63* (2013.01); *C07D 409/12* (2013.01)

(58) Field of Classification Search
CPC .. C07D 333/28; C07D 323/63; C07D 409/12; C07D 333/24
See application file for complete search history.

(56) References Cited

U.S. PATENT DOCUMENTS

| | | |
|---|---|---|
| 5,418,100 A | 5/1995 | Yu |
| 2002/0183395 A1 | 12/2002 | Argentieri |
| 2006/0160892 A1 | 7/2006 | Argentieri |
| 2006/0167248 A1 | 7/2006 | Tornoe et al. |
| 2006/0188445 A1 | 8/2006 | Ou et al. |
| 2009/0013757 A1 | 1/2009 | Gerits et al. |
| 2009/0023751 A1 | 1/2009 | Ou et al. |
| 2009/0118274 A1 | 5/2009 | Allen et al. |
| 2009/0143369 A1 | 6/2009 | Tornoe et al. |
| 2012/0071461 A1 | 3/2012 | Reich et al. |
| 2013/0231327 A1 | 9/2013 | Schunk et al. |
| 2014/0288135 A1 | 9/2014 | Eickhoff et al. |
| 2015/0126507 A1 | 5/2015 | Thies |
| 2016/0326186 A1 | 11/2016 | Simon et al. |

FOREIGN PATENT DOCUMENTS

| | | | |
|---|---|---|---|
| DE | 102010007281 A1 | 8/2011 | |
| EP | 0957099 A2 | 11/1999 | |
| EP | 2119476 A2 | 11/2009 | |
| EP | 2871181 A1 | 5/2015 | |
| EP | 3138833 A1 | 3/2017 | |
| WO | 2002048131 A1 | 6/2002 | |
| WO | 2004060281 A2 | 7/2004 | |
| WO | 2004082677 A1 | 9/2004 | |
| WO | 2005087754 A1 | 9/2005 | |
| WO | WO-2005087754 A1 * | 9/2005 | ........... C07D 265/06 |
| WO | 2006029623 A1 | 3/2006 | |
| WO | 2007/062308 A2 | 5/2007 | |
| WO | 2007087424 A2 | 8/2007 | |

(Continued)

OTHER PUBLICATIONS

Chemical Abstract Service, STN Database, Registry No. 1326062-68-3 [Entered STN: Aug. 31, 2011]. (Year: 2011).*
European Patent Office, European Search Report for European Patent Application No. 19179900.6, dated Sep. 26, 2019.
Matthews et al, "Design and Synthesis of Indane-ureido-thioisobutyric acids: A novel class of PPARalpha agonists", Biorganic & Medicinal Chemistry Letters, vol. 17, No. 24, Oct. 17, 2007, pp. 6773-6778.

(Continued)

*Primary Examiner* — Amanda L. Aguirre
(74) *Attorney, Agent, or Firm* — Duane Morris LLP (57) ABSTRACT

The present invention discloses novel compounds which are useful as potassium channel openers, in particular as openers of the Kv7.4 potassium channel. The novel compounds are compounds according to formula I,

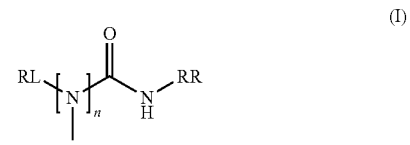

wherein
n=0 or 1,
RL is a substituent selected from the group consisting of unsubstituted or substituted cycloalkyl groups, in particular bicycloalkyl groups, unsubstituted or substituted phenyl groups, unsubstituted or substituted thienyl groups or cyclopentathienyl groups, and unsubstituted or substituted indanyl groups, which optionally contain heteroatoms, and
RR is a substituent selected from the group consisting of unsubstituted or substituted phenyl groups or unsubstituted or substituted benzyl groups, which optionally contain heteroatoms,
or a stereoisomer, a tautomer, a prodrug or a salt, preferably pharmaceutically acceptable salt thereof.

12 Claims, 3 Drawing Sheets

(56) References Cited

FOREIGN PATENT DOCUMENTS

| WO | 2007138112 A2 | | 12/2007 | |
|---|---|---|---|---|
| WO | 2008/100635 A1 | | 8/2008 | |
| WO | 2009015667 A1 | | 2/2009 | |
| WO | WO-2009015667 A1 | * | 2/2009 | ......... A61K 31/5375 |
| WO | 2009052062 A1 | | 4/2009 | |
| WO | 2009075874 A1 | | 6/2009 | |
| WO | 2010108651 A1 | | 9/2010 | |
| WO | 2011085351 A2 | | 7/2011 | |
| WO | WO-2011085351 A2 | * | 7/2011 | .............. A61P 25/00 |
| WO | 2012038081 A1 | | 3/2012 | |
| WO | 2012/022792 A1 | | 2/2013 | |
| WO | 2013126856 A1 | | 8/2013 | |
| WO | 2014052914 A1 | | 4/2014 | |
| WO | 2014079850 A1 | | 5/2014 | |
| WO | WO-2014079850 A1 | * | 5/2014 | ........... C07D 237/08 |
| WO | 2014191822 A1 | | 12/2014 | |
| WO | 2015067575 A1 | | 5/2015 | |
| WO | 2016127123 A2 | | 8/2016 | |
| WO | 2017131221 A1 | | 8/2017 | |

OTHER PUBLICATIONS

Fotsch C et al., "Synthesis and Structure-Activity Relationships of Trisubstituted Phenyl Urea Derivatives as Neuropeptide Y5 Receptor Antagonists", Journal of Medicinal Chemistry, vol. 44, No. 14, Jan. 1, 2001, pp. 2344-2356.
Database Registry, Chemical Abstracts Service, Aug. 24, 2008, XP002768474, Database Accession No. 1043292-24-5.
Database Registry, Chemical Abstracts Service, Apr. 5, 2008, XP002768475, Database Accession No. 671181-81-0.
Extended European Search Report in corresponding European Patent Application No. 17158326.3, 13 pages, Apr. 5, 2017.
Invitation to Pay Additional Fees and Partial International Search in corresponding International Patent Application No. PCT/EP2018/054820, 25 pages, dated Apr. 18, 2018.
Yu, Haibo, et al., "Discovery, Synthesis, and Structure-Activity Relationship of a Series of N-Aryl-bicyclo[2.2.1] heptane-2-carboxamides: Characterization of ML213 as a Novel KCNQ2 and KCNQ4 Potassium Channel Opener", ACS Chemical Neuroscience, vol. 2, No. 10, Oct. 19, 2011, pp. 572-577.
Herrington, et al. "Identification of Novel and Selective KV2 Channel Inhibitors", Molecular Pharmacology, vol. 80, No. 6, Dec. 1, 2011.
International Search Report and Written Opinion issued in corresponding PCT/EP2018/054820, dated Nov. 14, 2018, 27 pages.
Calderone, et al., "New Amido Derivatives as Potential BKCa Potassium Channel Activators. X1", European Journal of Medicinal Chemistry, vol. 43, No. 4, Apr. 1, 2008, pp. 792-799.
Calderone, et al. "Heterocyclic Analogs of Benzanilide Derivatives as Potassium Channel Activators. IX", European Journal of Medicinal Chemistry, Editions Scientifique Elsevier, vol. 41, No. 6, Jun. 1, 2006, pp. 761-767.
Cheung, et al., "Discovery of a Series of 2-Pheyl-N-(2-(pyrrolidin-1-yl) phenyl) acetamides as Novel Molecular Switches that Modulate Moves of K v 7.2 (KCNQ2) Channel Pharmacology: Identification of (S)-2-Phenyl-N-(2-(pyrrolidin-1-yl)phenyl)butanamide . . . ," Journal of Medicinal Chemistry, vol. 55, No. 15, Jul. 26, 2012, pp. 6975-6979.
Matthews, et al., "Design and Synthesis of indane-ureido-thioisobutyric acis: A novel class of PPARs agonists", Science Direct, Bioorganic & Medicinal Chemistry Letters 17 (2007) 6773-6778, Oct. 17, 2007.
Fotsche, et al., "Synthesis and Structure—Activity Relationships of Trisubsituted Phenyl Urea Derivatives as Neuropeptide Y5 Receptor Antagonists", J. Med. Chem 2001, 44, 2344-2356, Oct. 24, 2000.
European Examination Report, Communication pursuant to Article 94(3) EPC, dated Jan. 3, 2020, 6 pages.
Japanese Patent Office, Japanese Patent Application No. 2019-567399; Office Action dated Jun. 30, 2020 (w/ English translation).
Mexican Institute of Industrial Property, Mexican Patent Application No. MX/a/2019/010169; Office Action dated Jul. 15, 2020 (w/English translation).
Instituto Nacional De Propiedad Industrial—INAPI—Chile; Expert Examiner Report dated Nov. 13, 2020, for Chilean Patent Application No. 201902445 (filed Aug. 26, 2019).

* cited by examiner

COMPOUNDS USEFUL AS POTASSIUM CHANNEL OPENERS

PRIORITY CLAIM AND CROSS REFERENCE

The present application is a National Stage Application, filed under 35 U.S.C. 371, of International Patent Application No. PCT/EP2018/054820, filed on Feb. 27, 2018 and published as WO 2018/158256, which claims the priority of European Patent Application No. EP 17158326.3, filed on Feb. 28, 2017.

The present invention relates to novel compounds which are useful as potassium channel openers, in particular as openers of the Kv7.4 potassium channel. The present invention also relates to medicaments and pharmaceutical compositions comprising these compounds and to their use in human medicine and veterinary medicine.

It is estimated that approximately 10% of the population of the industrialized nations is affected by hardness of hearing. The vast majority of these cases can be attributed to a so-called sensorineural hearing loss which is characterized initially by a high frequency hearing loss affecting the ability to hear and understand speech. This sensorineural hearing loss or sensorineural deafness results mainly from damage of cells in the inner ear known as "hair" cells. These highly complex sensory cells detect the sound vibrations which are passed from outside, via the ear drum and the bones of the middle ear, to the cochlea. These sensory hair cells are located in the so-called organ of Corti.

Mammals are equipped with two quite different types of hair cells, namely the inner hair cells (IHCs) and the outer hair cells (OHCs). IHCs are the actual receptor cells of hearing, connected to the afferent nerves, while OHCs serve to mechanically pre-amplify the sound vibrations that reach the inner ear. This process, the "cochlear amplification", is crucial to the sensitivity and the high frequency resolution of mammalian hearing. As a consequence, many cases of hearing loss have their origin in a dysfunction or a loss of OHCs.

In this context, it is known that, as in other parts of the body of mammals, potassium channels play an important role for the normal function of cells, here of OHCs. A major pathway for $K^+$ exit from outer hair cells is represented by potassium channel Kv7.4. This channel is highly expressed in sensory outer hair cells (OHCs) in the organ of Corti. This fact, together with other research results, suggests that potassium channels, and in particular Kv7.4 is a promising target for the prophylaxis and the treatment of hearing loss.

At the time being hearing loss normally has to be treated with hearing aids, which amplify sound at preset frequencies to overcome a hearing loss in that range. In another approach, hearing loss has to be treated with cochlear implants which stimulate cochlear nerves directly.

As already mentioned above potassium channels are found in most cell types and control a wide variety of cell functions. Therefore, compounds which are potassium channel openers can be important for the prophylaxis or treatment of a wide variety of disorders. In this context, potassium channel Kv7.4, as mentioned above, is considered to play a critical role in the regulation of neuronal excitability.

Disorders associated with aberrant potassium channel activity are considered to be neurodegenerative disorders of various origins, e.g. Alzheimer's disease, Parkinson's disease and others. Further disorders are neurological conditions such as epilepsy or cognitive and psychiatric disorders like depression, mania and schizophrenia.

Other important disorders are various kinds of pain, namely neuropathic pain, chronic pain, acute pain, and headaches such as migraine and the like.

There are also indications that other disorders can be a target of compounds which have the function of a potassium channel opener. E.g. it is speculated that an activation of potassium channel Kv7.4 can be useful in cardioprotection.

Therefore, it is an object of the present invention to provide a novel group of compounds which are capable to deal with disorders associated with aberrant potassium channel activity in mammals, namely in prophylaxis or therapy. Preferably, but not necessarily, said disorder to be treated is an inner ear hearing loss after damage or loss of sensory hair cells in an organ of corti.

The present invention provides novel compounds represented by the general formula (I):

(I)

wherein
n=0 or 1,
RL is a substituent selected from the group consisting of unsubstituted or substituted cycloalkyl groups preferably bicycloalkyl groups, unsubstituted or substituted phenyl groups, unsubstituted or substituted thienyl groups or cyclopentathienyl groups and unsubstituted or substituted indanyl groups, which optionally contain heteroatoms, and
RR is a substituent selected from the group consisting of unsubstituted or substituted phenyl groups or unsubstituted or substituted benzyl groups, which optionally contain heteroatoms,
or a stereoisomer, a tautomer, a prodrug or a salt, preferably pharmaceutically acceptable salt thereof.

Compounds of formula (I) wherein said hetero atom is sulfur (S) are preferred.

According to the invention RL preferably is selected from cycloalkyl groups or bicycloalkyl groups comprising 5 to 10 C-atoms, in particular 6 to 8 C-atoms.

In other embodiments of the invention it is preferred that RL is selected from phenyl groups which are preferably substituted with at least one F-atom or Cl-atom.

According to another preferred group of inventive compounds RL is a substituent selected from thienyl groups or cyclopentathienyl groups which are preferably substituted with at least one F-atom or Cl-atom.

In other preferred embodiments of the inventive compounds RL is selected from indanyl groups which are preferably substituted with a least one F-atom or Cl-atom.

According to the invention RR is preferably a substituent selected from the group consisting of substituted phenyl groups or substituted benzyl groups. These preferred substituents selected as RR can also be substituted. As a consequence, in a first group of preferred embodiments, these substituents are selected from a (first) group consisting of F, $SF_5$, $CF_3$, and $OCF_3$, wherein $SF_5$ is further preferred as said substituent. In a second group of preferred embodiments, these substituents are selected from a (second) group consisting of dimethylamino-, pyrrolidino-, and morpholino-.

Considering now the groups and substituents which are preferred to be used as substituents RL and RR, respectively, different groups of preferred compounds according to the invention can be defined and mentioned. These groups are as follows:

- inventive compounds are preferred, if in these compounds substituent RL is selected from a phenyl group or a cycloalkyl group or a cyclopentathienyl group or an indanyl group, and if in these compounds substituent RR is substituted with a substituent from the above mentioned first group of substituents.
- inventive compounds are preferred, if in these compounds substituent RL is a thienyl group, and if in these compounds substituent RR is substituted with a substituent from the above mentioned first group or from the above mentioned second group of substituents.
- inventive compounds are preferred, if in these compounds substituent RL is selected from a cycloalkyl group or a bicycloalkyl group and if substituent RR is substituted with a substituent from the above mentioned second group of substituents.

According to the invention the following compounds are preferred, namely
(1R,2R,4S)-rel-N-(3-(pentafluorosulfanyhbenzyl)bicyclo[2.2.1]heptane-2-carboxamide
(1S,2S,4R)—N-(3-(pentafluorosulfanyl)benzyl)bicyclo[2.2.1]heptane-2-carboxamide
(1R,2R,4S)-rel-N-(3-(trifluormethypenzyl)bicyclo[2.2.1]heptane-2-carboxamide
(1R,2R,4S)-rel-N-(3-(trifluoromethoxy)benzyl)bicyclo[2.2.1]heptane-2-carboxamide
(1S,2S,4R)—N-(3-(trifluoromethyl)benzyl)bicyclo[2.2.1]heptane-2-carboxamide
(1S,2S,4R)—N-(3-(trifluoromethoxy)benzyl)bicyclo[2.2.1]heptane-2-carboxamide
(1S,2R,4R)-rel-2-(bicyclo[2.2.1]heptane-2-yl-N-(2-methyl-4-(pyrrolidin-1-yl-phenyl)acetamide
(1S,2R,4R)-2-(bicyclo[2.2.1]heptane-2-yl-N-(2-methyl-4-(pyrrolidin-1-yl-phenyhacetamide
(1S,2R,4R)-rel-2-(bicyclo[2.2.1]heptane-2-yl-N-(2,6-dimethyl-4-(dimethylamino-phenyl)acetamide
(1S,2R,4R)-2-(bicyclo[2.2.1]heptane-2-yl-N-(2,6-dimethyl-4-(dimethylamino-phenyl)acetamide
(1S,2R,4R)-rel-2-(bicyclo[2.2.1]heptane-2-yl-N-(2,6-dimethyl-4-(pyrrolidin-1-yl-phenyl)acetamide
(1S,2R,4R)-2-(bicyclo[2.2.1]heptane-2-yl-N-(2,6-dimethyl-4-(pyrrolidin-1-yl-phenyl)acetamide
(1S,2R,4R)-rel-2-(bicyclo[2.2.1]heptane-2-yl-N-(2-methyl-4-(dimethylamino-phenyl)acetamide
(1S,2R,4R)-2-(bicyclo[2.2.1]heptane-2-yl-N-(2-methyl-4-(dimethylamino-phenyl)acetamide,
wherein the following compounds are further preferred:
(1R,2R,4S)-rel-N-(3-(pentafluorosulfanyhbenzyl)bicyclo[2.2.1]heptane-2-carboxamide
(1S,2S,4R)—N-(3-(pentafluorosulfanyl)benzyl)bicyclo[2.2.1]heptane-2-carboxamide
(1S,2S,4R)—N-(3-(trifluoromethyl)benzyl)bicyclo[2.2.1]heptane-2-carboxamide
(1S,2S,4R)—N-(3-(trifluoromethoxy)benzyl)bicyclo[2.2.1]heptane-2-carboxamide
(1S,2R,4R)-2-(bicyclo[2.2.1]heptane-2-yl-N-(2-methyl-4-(pyrrolidin-1-yl-phenyhacetamide
(1S,2R,4R)-2-(bicyclo[2.2.1]heptane-2-yl-N-(2,6-dimethyl-4-(dimethylamino-phenyl)acetamide
(1S,2R,4R)-2-(bicyclo[2.2.1]heptane-2-yl-N-(2,6-dimethyl-4-(pyrrolidin-1-yl-phenyl)acetamide
(1S,2R,4R)-2-(bicyclo[2.2.1]heptane-2-yl-N-(2-methyl-4-(dimethylamino-phenyl)acetamide.

According to the invention the following compounds are also preferred, namely
p-Chloro-N-(4-trifluoromethoxy)benzyl)benzamide
p-Chloro-N-(4-(pentafluorosulfanyl)benzyl)benzamide
p-Fluoro-N-(4-trifluoromethoxy)benzyl)benzamide
p-Fluoro-N-(4-(pentafluorosulfanyl)benzyl)benzamide
p-Chloro-N-(4-(trifluoromethyl)benzyl)benzamide
p-Fluoro-N-(4-(trifluoromethyl)benzyl)benzamide,
wherein the following compounds are further preferred:
p-Chloro-N-(4-(pentafluorosulfanyl)benzyl)benzamide
p-Fluoro-N-(4-(pentafluorosulfanyl)benzyl)benzamide.

According to the invention the following compounds are also preferred, namely
5-Chloro-N-(4-trifluoromethoxy)benzyhthiophene-2-carboxamide
5-Fluoro-N-(4-trifluoromethoxy)benzyl)thiophene-2-carboxamide
5-Chloro-N-(4-(pentafluorosulfanyhbenzyhthiophene-2-carboxamide
5-Fluoro-N-(4-(pentafluorosulfanyhbenzyhthiophene-2-carboxamide
5-Fluoro-N-(4-(trifluoromethyl)benzyl)thiophene-2-carboxamide
5-Chloro-N-(4-(trifluoromethyl)benzyl)thiophene-2-carboxamide
N-(2,6-dimethyl-4-(pyrrolidin-1-yl)-phenyl)-2-(thiophene-2-yl)acetamide
N-(2-methyl-4-(pyrrolidin-1-yl)-phenyl)-2-(thiophene-2-yl)acetamide
N-(2,6-dimethyl-4-(pyrrolidin-1-yl)phenyl)-2-(5-chloro-thiophene-2-yl)acetamide
N-(2-methyl-4-(pyrrolidin-1-yl)-phenyl)-2-(5-chloro-thiophene-2-yl)acetamide
N-(2,6-dimethyl-4-(pyrrolidin-1-yl)-phenyl)-2-(5-fluoro-thiophene-2-yl)acetamide
N-(2-methyl-4-(pyrrolidin-1-yl)-phenyl)-2-(5-fluoro-thiophene-2-yl)acetamide
N-(2,6-dimethyl-4-(dimethylamino-1-yl)-phenyl)-2-(thiophene-2-yl)acetamide
N-(2-methyl-4-(dimethylamino-1-yl)-phenyl)-2-(thiophene-2-yl)acetamide
N-(2,6-dimethyl-4-(dimethylamino-1-yl)phenyl)-2-(5-chloro-thiophene-2-yl)acetamide
N-(2-methyl-4-(dimethylamino-1-yl)-phenyl)-2-(5-chloro-thiophene-2-yl)acetamide
N-(2,6-dimethyl-4-(dimethylamino-1-yl)-phenyl)-2-(5-fluoro-thiophene-2-yl)acetamide
N-(2-methyl-4-(dimethylamino-1-yl)-phenyl)-2-(5-fluoro-thiophene-2-yl)acetamide
N-(2,6-dimethyl-4-(morpholino-1-yl)-phenyl)-2-(thiophene-2-yl)acetamide
N-(2,6-dimethyl-4-(morpholino-1-yl)-phenyl)-2-(5-fluoro-thiophene-2-yl)acetamide
N-(2,6-dimethyl-4-(morpholino-1-yl)-phenyl)-2-(5-chloro-thiophene-2-yl)acetamide
(S)-3-(3,4-difluorophenyl)-1-(2-chloro-5,6-dihydro-4H-cyclopenta[b]thiophen-6-yl)-1-methylurea,
(S)-3-(3-pentafluorosulfanylphenyl)-1-(2-chloro-5,6-dihydro-4H-cyclopenta[b]thiophen-6-yl)-1-methylurea
wherein the following compounds are further preferred:
5-Chloro-N-(4-(pentafluorosulfanyl)benzyl)thiophene-2-carboxamide
5-Fluoro-N-(4-(pentafluorosulfanyhbenzyhthiophene-2-carboxamide N-(2,6-dimethyl-4-(pyrrolidin-1-yl)phenyl)-2-(5-chloro-thiophene-2-yl)acetamide (S)-3-(3,4-difluorophenyl)-1-(2-chloro-5,6-dihydro-4H-cyclopenta[b]thiophen-6-yl)-1-methylurea (S)-3-(3-pentafluorosulfanylphenyl)-1-(2-chloro-5,6-dihydro-4H-cyclopenta[b]thiophen-6-yl)-1-methylurea According to the invention the following compounds are also preferred, namely (S)-3-(3,4-difluorophenyl)-1-(2,3-dihydro-1H-inden-1yl)-1-methylurea (S)-3-(3,4-difluorophenyl)-1-(5-chloro-2,3-dihydro-1H-inden-1yl)-1-methylurea (S)-3-(3,4-difluorophenyl)-1-(5-fluoro-2,3-dihydro-1H-inden-1yl)-1-methylurea, (S)-1-(5-chloro-2,3-dihydro-1-H-inden-1-yl)-1-methyl-3-(3-pentafluorosulfanylphenyhurea wherein the following compounds are further preferred:

(S)-3-(3,4-difluorophenyl)-1-(5-chloro-2,3-dihydro-1H-inden-1yl)-1-methylurea (S)-1-(5-chloro-2,3-dihydro-1-H-inden-1-yl)-1-methyl-3-(3-pentafluorosulfanylphenyhurea.

The use of the inventive compounds for the therapy or prophylaxis of a disorder associated with aberrant potassium channel activity in mammals is preferred. In particular, according to the present invention, said disorder to be treated is an inner ear hearing loss after damage or loss of sensory hair cells in an organ of Corti.

As a consequence, the invention further provides a pharmaceutical composition or medicament comprising:

at least one inventive compound as claimed and defined above, and a pharmaceutically acceptable carrier or diluent.

Finally, the invention provides a method for treating a disorder in a mammal in need of such treatment, wherein the disorder comprises a disorder associated with aberrant potassium channel activity, in particular an inner ear hearing loss after damage or loss of sensory hair cells in an organ of Corti, and the method comprises administering to said mammal a therapeutically effective amount of the compound as claimed and as defined above.

In particular, the above-mentioned mammal is a human.

It is further preferred according to the invention, if the above-mentioned inventive composition or medicament not only comprises at least one of the inventive compounds, but also at least one additional active pharmaceutical ingredient. Such combination compositions or combination medicaments can be used in the inventive method for treating at least one disorder simultaneously or at least two disorders in parallel. Said additional active pharmaceutical ingredients can be e.g. compounds used as a standard medication for a certain disorder. Referring to disorders of the inner ear, in an inventive composition or medicament the inventive compounds preferably can be combined with a standard drug for treating sudden deafness (German: Hörsturz), e.g. with Dexamethasone.

The terms used in the claims and in the overall description are defined as follows.

The term "straight chain" as used herein, means a chemical structure in the form of an unbranched chain of atoms in a molecule with no attached side chains. Preferably said (unbranched) chain is an open chain. In contrast to that a "branched" structure includes one or more side chains attached to a chain of atoms in a molecule.

The term "substituted", as used herein, means that anyone or more hydrogens in the corresponding groups is replaced by another atom or group. E.g. "substituted cycloalkyl" refers to an cycloalkyl group in which one or more hydrogens are substituted, e.g. by halogen, hydroxy, or other atoms or groups. "Halogen" refers to fluorine, chlorine, bromine and iodine.

The term "alkyl" refers to (straight chain or branched chain) hydrocarbon groups of 1 to 20 carbon atoms, preferably 1 to 6 carbon atoms. In general, herein the terms C1, C2, C6, C20 and the like refer to the number of C-atoms (carbon atoms) present in the corresponding groups. Example alkyl groups include, but are not limited to, methyl, ethyl, propyl (e.g., n-propyl and isopropyl), butyl (e.g., n-butyl, isobutyl, t-butyl), and pentyl (e.g., n-pentyl, isopentyl, neopentyl).

The term "cycloalkyl" refers to a saturated cyclic hydrocarbon ring system. Exemplary groups include cyclopropyl, cyclobutyl, cyclopentyl, cyclohexyl, cycloheptyl, cyclooctyl, cyclodecyl, ad-amantyl and others.

The term "heteroatom" shall include oxygen, sulphur and nitrogen.

The definition of compounds according to the invention includes all possible "stereoisomers" and their mixtures. In particular, the racemic forms and the isolated optical isomers having the specified activity are included. The racemic forms can be resolved by physical methods, such as, for example fractional crystallisation, separation or crystallisation of diastereomeric derivatives or separation by chiral column chromatography. The individual optical isomers can be obtained from the racemates from the conventional methods, such as, for example, salt formation with an optically active acid followed by crystallisation.

The term "tautomers" refers to constitutional isomers of the inventive compounds that readily interconvert by a chemical reaction called tautomerisation. This reaction commonly results in the formal migration of a hydrogen atom or proton, accompanied by a switch of a single bond and adjacent double bond.

The inventive compounds of formula (I) may also have "prodrug" forms. Since prodrugs are known to enhance qualities of pharmaceuticals (e.g., solubility, manufacturing etc.) the compounds of the present invention may be delivered in prodrug form. "Prodrugs" are intended to include any covalently bonded carriers that release an active parent drug of the present invention in vivo when such prodrug is administered to a mammalian subject. Prodrugs include compounds of the present invention wherein e.g. a hydroxyl, amino or other group is bonded to any group that, when the prodrug is administered, cleaves to form a free hydroxyl, free amino or other, resp. Examples of prodrugs include, but are not limited to, acetate, formate, and benzoate derivates of alcohol and amine function groups in the compounds of the present invention. Various forms of prodrugs are well-known in the art. In this context, according to the invention, prodrug esters or prodrug peptides can be used as prodrug compounds. In certain cases, by coupling cell penetration-enhancing molecules such as, for example, biotin or maleimidopropionic acid, optionally via suitable spacer molecules, to the primary amino group, or by acylation of this amino group, it is possible to improve the bioavailability and thus the efficacy of the compounds according to the invention.

The phrase "pharmaceutically acceptable salts" refers to derivates of the disclosed compounds wherein the parent compound is modified by making acid or base salts thereof. Examples include, but are not limited to, mineral or organic acid salts of basic groups such as amines; and alkali and organic salts of acidic groups such as carboxylic acids. The pharmaceutically acceptable salts include the conventional non-toxic salts or the quaternary ammonium salts formed, for example, from non-toxic inorganic or organic acids. For example, such conventional non-toxic salts include those derived from inorganic acids such as hydrochloric, hydrobromic, sulphuric, phosphoric, and nitric; and the salts prepared from organic acids such as acetic, propionic and others.

The phrase "pharmaceutically acceptable carrier" and the phrase "pharmaceutically acceptable diluent" refer to media generally accepted in the art for the delivery of biologically active agents to animals, in particular mammals. Such media are well-known in the art.

The phrase "therapeutically effective amount" is intended to include an amount of a compound according to the present invention that is effective when administered alone or in combination. This phrase is also intended to include an amount of a combination of the claimed compounds that is effective to stimulate endogeneous regeneration of terminally differentiated cells in mammals. Preferably, said combination of compounds is a synergistic combination. Such synergy occurs when the effect of the compounds when administered in combination is greater than the additive effect of the compounds when administered alone as a single agent.

The terms "treating" or "treatment", as used herein, cover the treatment of a disorder-state in a mammal, particularly in a human, and include Preventing the disorder-state from occurring in a mammal, e.g. said mammal is predisposed to the disorder, but is not diagnosed to have that disorder, Inhibiting the disorder-state, i.e. stopping further development, and/or Relieving the disorder-state, i.e. improving the symptoms of the disorder.

According to the present invention, the claimed compounds and the claimed pharmaceutical composition/medicament may be administered to a mammal in different dosage forms. Preferred is a dosage form allowing direct administration of the compound to the damaged cells or tissues, e.g. into the cochlea of the mammal. Therefore, according to one embodiment of the invention non-oral dosage forms are preferred, in particular as injections. In these cases, administration onto or into the inner ear takes place, for example, transtympanally by injection into the middle ear, by application onto the round or oval window of the inner ear or by (direct) injection into the inner ear. In this context, e.g. pumps or similar devices may be employed. As a preferred dosage form also gels or similar materials have to be mentioned. E.g. said gels can be applied into the middle ear and release the active agent(s) over a longer period due to their jelly-like consistency.

It is also possible to apply the compounds (pharmaceutical composition, medicament) systemically, e.g. in an oral dosage form. These dosage forms include granules, powders, tablets or capsules, sirups, emulsions, suspensions etc.

All dosage forms can be manufactured by per se known techniques conventionally used in pharmaceutical procedures, for example by mixing, granulation or layering methods. The pharmaceutical compositions or medicaments may additionally be sterilized.

The exact dosage (therapeutically effective amount) of the compounds or the pharmaceutical composition/medicament according to the invention can be selected appropriately according to the recipient, its age and body weight, current clinical status, administration time, dosage form, method of administration, the compound actually employed and, if appropriate, other pharmaceuticals used.

A dose range, preferably an oral dose range, for an adult recipient may be selected between 0.01 to 10 mg/kg body weight, preferably 0.05 to 10 mg/kg body weight, more preferably 0.05 to 5 mg/kg body weight. In the treatment of an inner ear hearing loss after damage or loss of sensory hair cells in an organ of Corti the dosage can be related to the "number of inner ears treated" and/or to the "number of administration". The reason is, that a repeated administration of the compound/pharmaceutical composition over a time period, e.g. between a number of days and a number of weeks/months, preferably at intervals of some days (1 to 7 days), is appropriate. In these cases, the amount of active compound employed, preferably directly to the cochlea as described earlier, e.g. via infusion, should be in the range of from 0.5 µg to 1.0 mg per inner ear and administration.

The inventive compounds of formula (I) can be prepared by methods according to the prior art. As an example, the following general procedures are disclosed for providing inventive compounds being an " . . . amide" and an " . . . urea", respectively.

General Procedure for the Synthesis of Amides (Ureas)

1. The corresponding carbocyclic acid (0.5 mmol) was dissolved in 3 ml of dry dimethylformamide (DMF), and diisopropylethylamine (1.5 mmol) and coupling reagent HATU [O—N,N,N'',N''-tetramethyluronium-hexafluorophosphat] (0.55 mmol) were added. The mixture was stirred for 15 min and the corresponding amine (0.55 mmol) was added. The resulting reaction mixture was stirred for an additional time of 4-16 h, while the completion of the reaction was controlled by TLC (Thin Layer Chromatography) or LC-MS (Liquid Chromatography-Mass Spectrometry). The mixture was diluted with 25 ml ethyl acetate (EtOAc), washed 1-time with 20 ml brine, washed 1-time with 20 ml saturated $NaHCO_3$ solution, washed 3 times with 20 ml 5% citric acid solution and washed 1-time with 20 ml saturated $NaHCO_3$ solution again, dried over anhydrous $Na_2SO_4$, and concentrated in vacuo. The resulting residue was purified by flash chromatography (typically with petroleum ether-EtOAc system) and/or crystallization and/or reverse phase preparative HPLC, if necessary.

2. To a solution of the corresponding amine (0.5 mmol) in 2.5 ml dichloromethane, was added a solution of the corresponding isocyanate (0.5 mmol) in 2.5 ml of dichloromethane (dropwise with stirring). The mixture was stirred for 1 h (or longer, if necessary) and the progress of reaction was controlled by TLC or LC-MS. Then, the reaction mixture was diluted with 20 ml EtOAc, washed 1-time with 20 ml brine, washed 1-time with 20 ml saturated $NaHCO_3$ solution, washed 3 times with 20 ml 5% citric acid solution, washed 1-time with 20 ml saturated $NaHCO_3$ solution again, dried over anhydrous $Na_2SO_4$, and concentrated in vacuo. The resulting residue was purified by flash chromatography (typically with petroleoum ether-EtOAc system) and/or crystallization and/or reverse phase preparative HPLC, if necessary.

In the above procedure, commercially available isocyanates were used, or these isocyanates were prepared according to one of the following methods:

isocyanate synthesis 1

To a mixture of 5 ml dichloromethane and 5 ml water were sequentially added (corresponding) substituted aniline (0.5 mmol), $NaHCO_3$ (100 mg, 1.2 mmol) and 59 mg (0.2 mmol) of triphosgene. The resulting reaction mixture was vigorously stirred for 30 min, the dichloromethane layer was 2 times washed with 10 ml of brine, shortly dried over MgSO$_4$ and used as an isocyanate stock solution for the synthesis of the corresponding ureas.

isocyanate synthesis 2

(Corresponding) substituted aniline (0.5 mmol) was dissolved in 2.5 ml of dimethyl sulfoxide (DMSO) and carbonyldiimidazole (100 mg, 0.6 mmol) was added. The solution was stirred for 2 h at room temperature and used directly for the synthesis of corresponding ureas.

Pharmacological Results

Kv7.4 activation was measured by using a functional Kv7.4 cell line and a thallium-sensitive fluorescent dye at FLIPRTetra (High-Throughput Cellular Sceening System of Molecular Devices, LLC, USA). The assay principle is based on the permeability of potassium channels to thallium. Thallium entry was measured in CHO cells (Chinese hamster ovary cells) stably transfected with Kv7.4 encoding gene. The cells were loaded with the Thallos™ dye (TEFLABS, cat. #0913), which at this stage is a pro-fluorescent dye. After channel activation, with an extracellular solution containing thallium, thallium ions move down concentration gradient through open potassium channels across cell membrane. When thallium ion binds to Thallos™ dye, it emits a bright fluorescent emission at 515 nm upon an excitation at 490 nm. Importantly, the fluorogenic signal measured quantitatively reflects the activity of ion channels that are permeant to thallium.

Experiments were performed in 384-well plates according to the following procedure:
1. Seed cells at 10.000 c/w in 384-well plates black walled clear bottom.
2. Twenty-four hours after seeding, discharge medium manually and add 20 μL/w of 0.5× Thallos™ sensitive dye prepared according to manufacturer instructions.
3. Incubate cells 1 h at room temperature.
4. Inject off-line 5 μL/well of test compounds 5×-concentrated in thallium free, chloride-free Tyrode's buffer (5 mM Potassium D-Gluconate, 130 mM Sodium D-Gluconate, 2 mM Calcium D-Gluconate, 5 mM NaHCO$_3$, 1 mM Magnesium D-Gluconate, 20 mM HEPES, pH7.4) with 2.5% DMSO (final DMSO is 0.5%).
5. After 10 minutes of incubation inject 25 μL/well of 2×-concentrated thallium EC20 (5 mM) at FLIPRTetra and monitor the kinetic response for 120 seconds.

The effect of the inventive test compounds was measured as percent activity vs the reference opener ML213 at EC100 (100 μM) and EC50 values were calculated accordingly. Compounds of the invention were active as Kv7.4 openers with an EC50 comprised between 10 nM and 5 μM.

In Vivo Experiments

The inventive compounds were also tested in vivo. In this context, for repeated recording of the Compound Action Potential (CAP) of the auditory nerve, guinea pigs were bilaterally implanted with a permanent gold electrode at the round window niche. The round window is an opening from the middle ear into the inner ear. The gold electrodes were connected to a miniature plug on the skull. During the experiments, audiograms were determined between 0.5 and 45.6 kHz, at a resolution of 8 steps per octave. An automated threshold search algorithm was applied.

After a baseline audiogram was measured, the animals were pretreated with an inventive compound, as an ion channel activator, via local application to the middle ear. The corresponding solution of the inventive compound was removed after an exposure time, e. g. after 2 hours. Then, the middle ear was rinsed and dried out before CAP recordings were performed to assess threshold shifts.

Then, deafness was induced with the Guinea pigs by local application to the middle ear of a mixture of at least one ototoxic agent and at least one inventive compound. E. g. kanamycin, furosemide or mixtures of these compounds can be used as ototoxic agents.

The resulting CAP response thresholds were compared to ears which were exposed to the ototoxic agents alone.

With these experiments it could be shown that the exposure to the ototoxic agents alone, e. g. exposure to kanamycin or to furosemide or to mixtures of these compounds, revealed severe cochlear hearing loss. In contrast, if these ototoxic agents are applied together with at least one of the inventive compounds, there is a significant reduction of hearing loss, compared to the hearing loss with the ototoxic agents alone.

Further details of the in vivo experiments are as follows. In this context the drawings show

Figure 1:
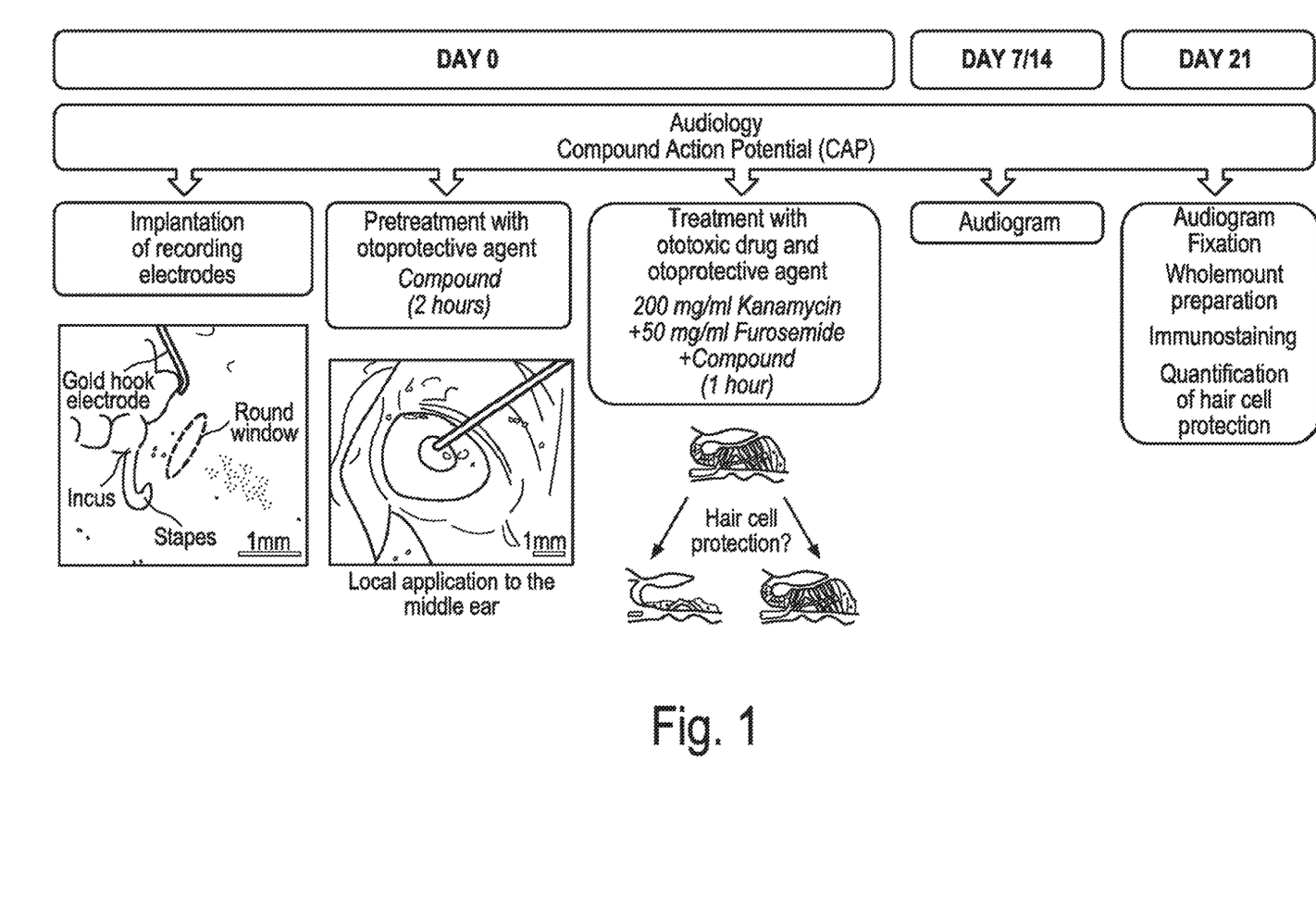
FIG. 1: Schematic illustration of the experimental design to investigate otoprotective compounds in an ototoxic drug-induced hearing loss model in vivo.

The typical workflow of the in vivo experiments is shown in FIG. 1. All animals received care in accordance with the standards described by the German law on Protecting Animals' (Tierschutzgesetz) and with the European Directive 2010/63/EU for the protection of animals used for experimental purposes. Experiments were approved by the local authorities (Application HN03/15).

All procedures were performed under anesthesia using a mixture of Fentanyl, Midazolam and Medetomidine. During surgery and measurements animals were kept on a 37° C. heating pad. For repeated recording of the Compound Action Potential (CAP) of the auditory nerve, guinea pigs were bilaterally implanted with a permanent gold electrode at the round window (RW) niche connected to a miniature plug on the skull. Audiograms were determined between 0.5 and 45.6 kHz, at a resolution of 8 steps per octave. An automated threshold search algorithm was applied.

After a baseline audiogram was measured, animals were pretreated with an ion channel activator, in this case with ACOU001, via local application to the middle ear. ACOU001 (internal designation of the applicant) is 5-Chloro-N-(4-(pentafluorosulfanyl)benzyl)thiophene-2-carboxamide.

The chemical structure of this compound ACOU001 is as follows:

The solution containing ACOU001 was removed after 2 hours and the middle ear rinsed and dried out before CAP recordings were performed to assess threshold shifts. Guinea pigs were then deafened by local application to the middle ear using a mixture of 200 mg/ml kanamycin, 50 mg/ml furosemide and 100 μM ACOU001. CAP response thresholds were compared to ears which were exposed to the ototoxic agent alone. CAP recordings were performed 7, 14 and 21 days after this treatment. After the final measurement on day 21, animals were sacrificed, cochleae fixed by perfusion with 4% paraformaldehyde and prepared for immunohistological analysis to quantify hair cell (HC) protection.

Figure 2:
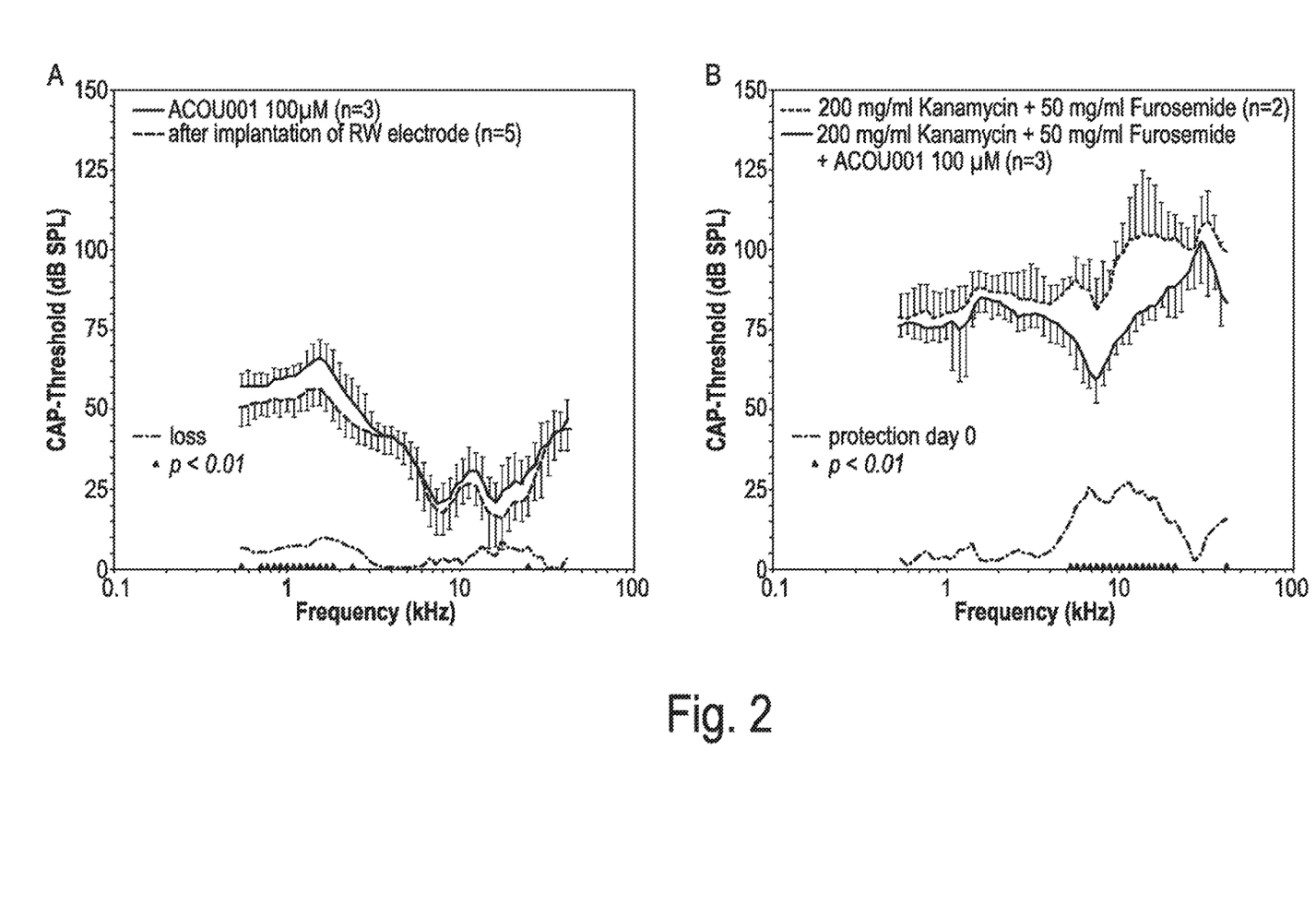
FIG. 2: Quantitative analysis of CAP responses on day 0. (A) CAP-threshold loss after pretreatment with ACOU001. (B) Otoprotection after local application of ACOU001 and kanamycin/furosemide in comparison to the treatment with the ototoxic drug alone.
Figure 3:
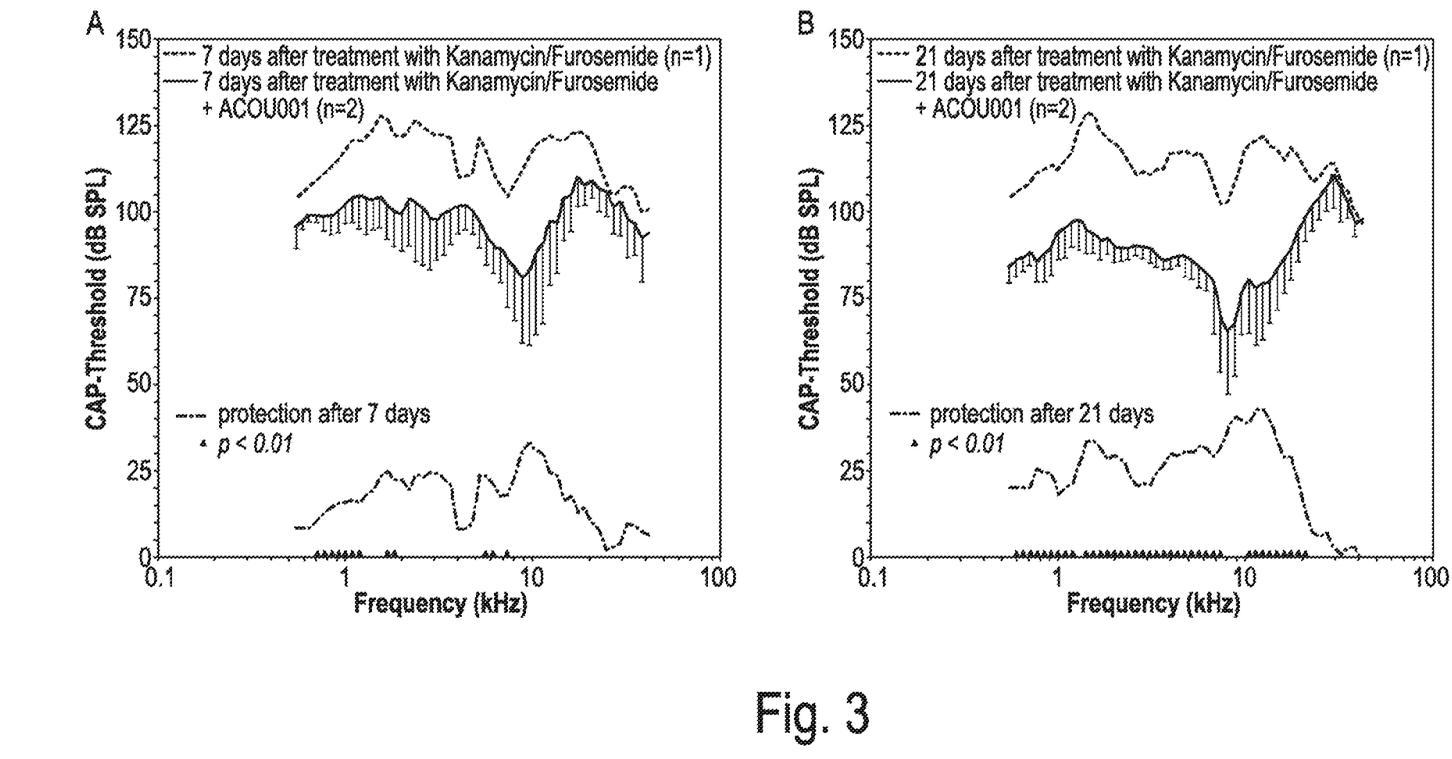
FIG. 3: Quantitative analysis of CAP responses at different observation time point. Otoprotection 7 days (A) and 21 days (B) after treatment with ACOU001 and kanamycin/furosemide in comparison to the treatment with the ototoxic drug alone.

The results obtained from this set of experiments are shown in FIGS. 2 and 3. Compared to the baseline CAP-thresholds in untreated ears (FIG. 2A, (middle) broken line), pretreatment with the compound ACOU001 ((upper) solid line) lead to a small, most likely conductive, hearing loss ((lower) dotdashed line: difference between upper and middle line). This conductive hearings loss might be explained by remaining fluid in the middle ear after local application. The remaining fluid impairs middle ear transmission at low frequencies (FIG. 2A, black triangles).

Exposure to kanamycin and furosemide (FIG. 2B, (upper) broken line) revealed severe pancochlear hearing loss. In contrast, application of ACOU001 together with the ototoxic drug ((middle) solid line) caused a significant reduction of hearing loss of 25 dB SPL (SPL: Sound Pressure Level) in mid to high frequencies (5-11 kHz) compared to the ototoxic drug alone (lower dotdashed line).

Seven days after administration of kanamycin and furosemide, profound hearing loss was recorded and remained permanent in the entire frequency range (PTS: Permanent Threshold Shift) over a duration of 21 days (FIG. 3A/B, upper broken line). CAP curves after treatment with kanamycin/furosemide plus ACOU001 also shifted to higher threshold levels after seven days but ameliorated after 21 days (FIG. 3A/B, middle solid line). In comparison to the one deafened animal, a significant reduction of hearing loss (25-40 dB SPL) at all frequencies was recorded after 21 days of co-treatment with the aminoglycoside kanamycin plus ACOU001 (FIG. 3B, lower dotdashed line).

Similar significant results (with hearing protections (reduction of hearing loss) of at least 20-30 dB SPL) are obtained during in vivo experiments with the compounds

(1R,2R,4S)-rel-N-(3-(pentafluorosulfanyl)benzyl)bicyclo[2.2.1]heptane-2-carboxamide (1S,2S,4R)—N-(3-(pentafluorosulfanyl)benzyl)bicyclo[2.2.1]heptane-2-carboxamide N-(2,6-dimethyl-4-(pyrrolidin-1-yl)phenyl)-2-(5-chlorothiophene-2-yl)acetamide

The invention claimed is:

1. A compound of formula I wherein
n=0,
RL is a substituent selected from the group consisting of unsubstituted bicycloalkyl groups, and substituted thienyl groups, wherein said thienyl groups are substituted with at least one F-atom or Cl-atom, and
RR is a substituted benzyl group, wherein said benzyl group comprises at least one substituent being SF$_5$,
or a stereoisomer, a tautomer, a prodrug or a pharmaceutically acceptable salt thereof.

2. The compound according to claim 1, wherein said bicycloalkyl groups selected as substituent RL comprise 5 to 10 C-atoms.

3. The compound according to claim 1, wherein said thienyl groups are substituted with at least one Cl-atom.

4. The compound according to claim 1, wherein said bicycloalkyl groups selected as substituent RL comprise 6 to 8 C-atoms.

5. The compound according to claim 1, wherein the compound is
(1R,2R,4S)-rel-N-(3-(pentafluorosulfanyl)benzyl)bicyclo[2.2.1]heptane-2-carboxamide, or
(1S,2S,4R)—N-(3-(pentafluorosulfanyl)benzyl)bicyclo[2.2.1]heptane-2-carboxamide.

6. The compound according to claim 1, wherein the compound is
5-Chloro-N-(4-(pentafluorosulfanyl)benzyl)thiophene-2-carboxamide or
5-Fluoro-N-(4-(pentafluorosulfanyl)benzyl)thiophene-2-carboxamide.

7. A pharmaceutically acceptable salt of the compound according to claim 1.

8. A pharmaceutical composition or medicament, comprising:
at least one compound according to claim 1, and
a pharmaceutically acceptable carrier or diluent.

9. A method of using the compound according to claim 1, comprising administering to a subject a pharmaceutically effective amount of the compound of claim 1 for use as a pharmaceutical composition or a medicament.

10. The method according to claim 9, wherein said use is for treating a disorder associated with aberrant potassium channel activity in mammals.

11. The method according to claim 10, wherein the disorder to be treated is an inner ear hearing loss after damage or loss of sensory hair cells in an organ of *Corti*.

12. The method according to claim 9, wherein said use is for prophylaxis of an inner ear hearing loss.

\* \* \* \* \*